United States Patent
Gaubicher et al.

(10) Patent No.: US 9,704,655 B2
(45) Date of Patent: Jul. 11, 2017

(54) COMPOUNDS HAVING A REDOX GROUP, USE THEREOF AS AN ELECTROLYTE ADDITIVE, ELECTROLYTE COMPOSITION, AND ELECTROCHEMICAL SYSTEMS CONTAINING SAME

(75) Inventors: Joel Gaubicher, Nantes (FR); Lenaic Madec, Gueret (FR); Audrey Bouvree, Saint Mars du Desert (FR); Philippe Blanchard, Saint Lambert la Potherie (FR); Bernard Lestriez, Nantes (FR); Thierry Brousse, La Chapelle sur Erdre (FR); Dominique Guyomard, Sautron (FR)

(73) Assignees: CENTRE NATIONAL DE LA RECHERCHE SCIENTIFIQUE, Paris (FR); UNIVERSITE DE NANTES, Nantes (FR)

( * ) Notice: Subject to any disclaimer, the term of this patent is extended or adjusted under 35 U.S.C. 154(b) by 790 days.

(21) Appl. No.: 14/116,397

(22) PCT Filed: May 10, 2012

(86) PCT No.: PCT/FR2012/051032
§ 371 (c)(1),
(2), (4) Date: May 8, 2014

(87) PCT Pub. No.: WO2012/153067
PCT Pub. Date: Nov. 15, 2012

(65) Prior Publication Data
US 2014/0302386 A1    Oct. 9, 2014

(30) Foreign Application Priority Data

May 12, 2011 (FR) .................. 11 54137

(51) Int. Cl.
| | |
|---|---|
| *C07F 17/02* | (2006.01) |
| *C09K 9/02* | (2006.01) |
| *C07D 333/34* | (2006.01) |
| *H01M 4/60* | (2006.01) |
| *H01G 11/58* | (2013.01) |
| *C07D 249/06* | (2006.01) |
| *H01M 10/05* | (2010.01) |
| *H01M 10/052* | (2010.01) |
| *H01M 10/0567* | (2010.01) |
| *H01G 5/18* | (2006.01) |
| *H01G 11/02* | (2013.01) |
| *H01G 11/60* | (2013.01) |
| *H01G 11/26* | (2013.01) |
| *H01G 11/62* | (2013.01) |

(52) U.S. Cl.
CPC .......... *H01G 11/58* (2013.01); *C07D 249/06* (2013.01); *C07D 333/34* (2013.01); *C07F 17/02* (2013.01); *C09K 9/02* (2013.01); *H01G 5/18* (2013.01); *H01G 11/02* (2013.01); *H01G 11/26* (2013.01); *H01G 11/60* (2013.01); *H01M 10/05* (2013.01); *H01M 10/052* (2013.01); *H01M 10/0567* (2013.01); *C09K 2211/1007* (2013.01); *C09K 2211/1011* (2013.01); *C09K 2211/1092* (2013.01); *H01G 11/62* (2013.01); *H01M 2300/0091* (2013.01); *Y02E 60/13* (2013.01)

(58) Field of Classification Search
CPC .......... H10G 11/64; H10G 2009/0007; H10G 2009/0025; H10G 9/035; H10G 9/038; H10G 9/145; H10G 9/155; H01M 6/168; H01M 10/0567; H01M 12/005; H01M 12/02; H01M 2300/0025
See application file for complete search history.

(56) References Cited

FOREIGN PATENT DOCUMENTS

| | | | |
|---|---|---|---|
| GB | 2467148 | | 7/2010 |
| JP | 2005-251683 | * | 9/2005 |
| JP | 2009-238945 | * | 10/2009 |

OTHER PUBLICATIONS

Klare et al, "Assembling p-type molecules on single wall carbon nanotubes for photovoltaic devices", Chem. Commun. 2009, May 2009, pp. 3705-3707.*
Le Goff et al, "facile and tunable functionalization of carbon nanotube electrodes with ferrocene by covalent coupling and pi-stacking interactions and their relevance to glucoe bio-sensing", Journal of Electroanalytical Chemistry, 641, Jan. 2010, pp. 57-63.*
Translation of the detailed decription for JP 2005-251683: Sep. 15, 2005.*
Translation of the detailed decription for JP 2009-238945: Oct. 15, 2009.*
Search Report dated 2012.

* cited by examiner

*Primary Examiner* — Carol M Koslow
(74) *Attorney, Agent, or Firm* — Ipsilon USA, LLP (57) ABSTRACT

The invention relates to compounds comprising a redox group, to the use thereof as an additive to an electrolyte composition, to an electrolyte composition including such an additive, and to electrochemical systems including such an electrolyte composition, in particular lithium or sodium batteries and supercapacitors having a double electric layer.

11 Claims, 2 Drawing Sheets

FIGURE 1

Number of cycles

COMPOUNDS HAVING A REDOX GROUP, USE THEREOF AS AN ELECTROLYTE ADDITIVE, ELECTROLYTE COMPOSITION, AND ELECTROCHEMICAL SYSTEMS CONTAINING SAME

RELATED APPLICATION

This application is a National Phase Application of PCT/FR2012/051032, filed on May 10, 2012, which in turn claims the benefit of priority from French Patent Application No.11 54137 filed on May 12, 2011, the entirety of which are incorporated herein by reference.

BACKGROUND

Field of the Invention:

The present invention relates to compounds comprising a redox group, to their use as additive in an electrolyte composition, to an electrolyte composition comprising said additive and to electrochemical systems comprising said electrolyte composition, in particular lithium or sodium batteries and electric double-layer supercapacitors.

Description of Related Art:

In a known way, batteries are composed of a positive electrode (cathode), generally a transition metal oxide (cobalt or manganese dioxide), and of a negative electrode made of graphite (anode), between which is placed a separator impregnated with an electrolyte consisting of a lithium or sodium salt in solution in a solvent chosen in order to optimize the transportation and the dissociation of the ions (in general a mixture of carbonates). A current collector is connected to the cathode in order to ensure the electrical connection.

Electrochemical systems having electric double-layer and/or pseudocapacitive storage, such as supercapacitors, are energy storage devices, the basic principle of which is based on the capacitive properties of the interface between a solid electron conductor and a liquid ion conductor. A supercapacitor is generally composed of two metal current collectors, generally made of aluminum, of two porous carbon-based electrodes impregnated with electrolyte, and of a porous separating membrane. Energy storage is carried out by distributing the ions of electrolyte in the vicinity of the surface of each electrode under the electrostatic influence of the applied voltage. A space charge region, known as electric double layer, with a thickness limited to a few nanometers and in which the relatively intense electric field (of the order of 10 kV·$\mu m^{-1}$) prevails, is thus created at the interfaces.

Electrochemical systems having faradaic electrodes, such as lithium batteries, exhibit good performances in terms of energy but are not very effective in terms of power. The reverse is the case for electrochemical systems having double-layer and/or pseudocapacitive storage, such as supercapacitors, for example. Furthermore, electrochemical systems having faradaic electrodes, such as lithium batteries or hybrid supercapacitors, for example, all operate by virtue of an electrode in which the electrode active material has to be (co)mixed beforehand with one or more polymers or deposited with/on the conducting agent or agents of the electrodes before assembling the electrochemical system, so as to obtain effective electrical contacts, a condition sine qua non for good performances of these systems. It is the stage of shaping the electrode.

Various methods have already been envisaged for improving the performances, in particular power, of these electrochemical systems.

Some authors, such as Qin Y. et al. (Journal of Power Sources, 2010, 195, 6888-6892), have tested the addition of 3,9-divinyl-2,4,8,10-tetraoxaspiro[5.5]undecane (TOS) to a base electrolyte in order to increase the lifetime and the thermal stability of lithium batteries comprising a negative electrode based on mesocarbon microbeads (MCMBs), on carbon fibers and on polyvinylidene fluoride (PVDF) dispersed in N-methyl-2-pyrrolidone on a copper sheet, a positive electrode based on Li[$Ni_{1/3}Co_{1/3}Mn_{1/3}$]$O_2$ (NCB), on carbon black and on Pilaf dispersed in N-methyl-2-pyrrolidone on an aluminum sheet, a separator made of microporous polypropylene and $LiPF_6$ as electrolyte. The authors indicate that the addition of TOS in a proportion of 1% by weight to the electrolyte improves the retention capacity of the battery (in operation at a temperature of 55° C.) and its thermal stability but that an amount of this same compound of greater than 0.5% brings about, on the other hand, a significant fall in the impedance.

Yu H. et al. (Electrochemical and Solid-State Letters, 2004, 7(11), A442-A446) have tested the use of vinyl ethylene carbonate as additive in an electrolyte based on propylene carbonate and on lithium bis(perfluoroethylsulfonyl)imide (LiBETI) in lithium batteries comprising either an anode prepared from a graphite powder or an anode prepared from MCMB. The presence of this additive in the electrolyte makes it possible to create a protective film at the surface of the electrode, so as to prevent the lithium ions from becoming inserted in the graphite and from damaging it, which has the consequence of improving the performance of the battery. However, the authors indicate that this effect is only observed with the battery comprising the electrode prepared from graphite powder but not with that in which the electrode was prepared from MCMB. This method is therefore not applicable to every type of carbon-based electrode and even less to any type of electrode.

Other methods employ redox shuttles, that is to say batteries in which the electrolyte comprises, as additive, a redox compound or a reactive polymer which, during the operation of the battery, plies between the two electrodes (Z. Chen et al., Electrochimica Acta, 2009, 54, 5605-5613), with the aim of preventing overcharges. Such redox compounds can, for example, be aromatic compounds, such as 1,4-di(tert-butyl)-2,5-dimethoxybenzene, (2,2,6,6-tetramethylpiperidin-1-yl)oxyl (TEMPO) or 2-(pentafluorophenyl)tetrafluoro-1,3,2-benzodioxaborole (PFPTFBB), or nonaromatic compounds, such as certain borated lithium salts, such as $Li_2B_{12}F_{12-x}H_x$ with x=1-12. However, the authors indicate that it remains difficult to find compounds which do not end up by decomposing and which remain effective over time. Furthermore, these compounds have to diffuse into the electrolyte in order to ensure redox reversibility. They are thus not localized at an electrode, which renders them incapable of delivering and/or accumulating high-power energy.

Finally, other methods provide for the functionalization of the carbon electrodes by organic groups of carboxylic or amino type, such as described, for example, by Lee et al. (Nature Nanotechnology, 2010, 5, 531-537), by sulfophenyl groups, as described by D. Pech et al. (Electrochemical and Solid-State Letters, 2008, 11, A202-A205), or by aromatic groups, for example of pyrene type, such as described in particular by C. Ehli et al. (JACS, 2006, 128, 11222-11231). However, these methods make it necessary to carry out the molecular functionalization of the electrode active material (graphite or carbon) before the assembling of the nonconventional electrodes, which thus necessitates an additional stage.

OBJECTS AND SUMMARY

The inventors thus set themselves the target of providing a solution which makes it possible to improve the power of electrochemical systems having faradaic electrodes and also the energy of pseudocapacitive and/or electric double-layer electrode systems and which is easy, rapid and simple to implement. In particular, the inventors set themselves the target of providing a solution which avoids any additional stage of shaping the electrode or recourse to a hybrid system comprising a battery electrode and a supercapacitor electrode.

The inventors have developed novel compounds comprising a redox group, the use of which, as additive in an electrolyte composition, makes it possible to overcome the disadvantages of the systems of the prior art and in particular makes it possible to improve the power of electrochemical systems having faradaic electrodes and also the energy of pseudocapacitive and/or electric double-layer electrode systems.

A first subject matter of the present invention is thus a compound of following formula (I):

A-(B)$_x$-Redox    (I)

in which:
A represents a group chosen from:
  i) groups capable of being chemisorbed at the surface of materials predominantly comprising hydroxyl functional groups, such as materials of oxide type;
  ii) groups capable of being chemisorbed at the surface of carbon-based materials or materials comprising a carbon-based additive;
x is 0 or 1,
B represents a connecting arm chosen from linear $C_1$-$C_{100}$ alkyl chains optionally comprising one or more heteroatoms, such as O, N or S, one or more functional groups, such as an amide or ester functional group, and/or one or more aromatic rings and/or one or more heterocycles; aromatic groups and heterocycles,
Redox represents a redox group comprising one or more redox functional groups.

The use of at least one compound of formula (I) in accordance with the invention as additive in an electrolyte composition of an electrochemical system results in an enhancement in the power and/or energy performances of said system without it being necessary to resort to an additional stage of shaping the electrodes and/or of functionalization.

In addition, the use of such an electrolyte composition exhibits the following advantages:
  it makes it possible to use all compositions of electrodes between battery and supercapacitor as the compound of formula (I) is present in the electrolyte composition;
  the power performances of the electrodes of batteries are enhanced;
  the energy performances of the electrodes of supercapacitors are enhanced;
  the energy and power performances of the electrodes of intermediate compositions are enhanced;
  versatility of the working potential, versatility of the molecules chosen and thus possibility of use of organic materials resulting from green chemistry (rhodizonate salts, for example).

According to the invention, the term "to chemisorb" means that bonds of chemical nature, either of covalent nature or by intermolecular forces, in particular π-stacking and/or of Van Der Waals type, are created between the group A and the carbon-based additives and/or the hydroxyl functional groups of materials participating in the composition of the electrode materials.

According to the invention, the groups A capable of being chemisorbed at the surface of the materials comprising hydroxyl functional groups are preferably chosen from groups comprising a hydroxyl functional group capable of condensing with the surface hydroxyl functional groups of the materials by an oxolation/olation reaction. Mention may more particularly be made, among such groups, of phosphonate, carboxylate, sulfonate and silane groups, and the like.

The groups A capable of being chemisorbed at the surface of carbon-based materials or materials comprising a carbon-based additive are preferably chosen from the aromatic derivatives of supramolecular chemistry, such as, for example, polycyclic hydrocarbons, such as pyrene, perylene, anthracene, triphenylene, coronene, fluorene and azulene groups, and the like.

The redox group of the compounds of formula (I) is preferably chosen from ferrocene (2,2,6,6-tetramethylpiperidin-1-yl)oxyl, porphyrin, oligothiophene, S-bithiophene-S-methyl, oligo-3,4-ethylenedioxythiophene (oligo-EDOT), oligopolyaniline (oligo-PANI), oligopyrrole, anthracene and catechol groups, rhodizonate salts, and the like.

The presence of a connecting arm in the compounds of formula (I) above is not obligatory; for this reason, the nature of the connecting arm B is not critical provided that it ensures a permanent connection between the group A and the redox group of the compounds of formula (I).

According to a preferred embodiment of the invention and when x=1, the connecting arm B of the compounds of formula (I) corresponds to one of the following formulae (B-1) to (B-3):

(B-1)

(B-2)

(B-3)

in which:
* represents the point of attachment of the connecting arm to the group A via a covalent bond;
** represents the point of attachment of the connecting arm to the redox group via a covalent bond;
n is an integer varying from 0 to 10;
m is an integer varying from 0 to 10.

According to a particularly preferred embodiment of the invention, B represents a connecting arm Chosen from:
a connecting arm of formula (B-1) with n=3 and m=0;
a connecting arm of formula (B-2) with n=3 and m=2;
a connecting arm of formula (B-3) with n=1 and m=1.

Preference is given, among the compounds of above formula (I), to the compounds of following formulae (I-1) to (I-3):

The compounds of formula (I) in accordance with the invention in which x=0 can be prepared by synthetic methods known to a person skilled in the art, by condensation of a precursor of a group A with a precursor of a redox group.

The compounds of formula (I) in accordance with the invention in which x=1 can also be prepared by synthetic methods known to a person skilled in the art, by condensation of a precursor of a group A (A-$L_1$) with a precursor of a connecting arm B ($L_2$-B-$L_3$) by an appropriate reaction which depends on the chemical nature of L. The intermediate compound of formula A-B-$L_3$ thus obtained can be condensed with a precursor of a redox group ($L_4$-Redox) by an appropriate reaction which depends on the chemical nature of L. The resulting compound is of general formula A-B-Redox. A similar process can be adopted in synthesizing $L_2$-B-Redox, which can react with A-$L_1$ to give A-B-Redox.

The compounds of formula (I) in accordance with the invention in which x=0, that is to say the compounds of A-Redox type, can be obtained in a similar way to that presented above for the compounds of formula (I) in which x=1, by connecting a precursor of a group A (A-$L_1$) and a precursor of a redox group ($L_4$-Redox) by an appropriate reaction which depends on the chemical nature of L. The resulting compound is of general formula A-Redox. The functional groups L are groups capable of reacting with one another to form a covalent bond. The reaction between the various groups L makes it possible to link together the precursors of the chemical groups A, B and Redox.

Mention may be made, as first example of a pair of functional groups L, of an azido group and an acetylene group which make possible the Huisgen reaction (Huisgen, R et al., Chem. Ber., 1967, 100, 2494; Huisgen, R et al., Chem. Ber., 1965, 98, 4014), according to one of the following reaction schemes:

In this scheme, R represents A or A-B and R' represents B or Redox.

The reaction can be carried out either in the presence of a compound derived from Cu(I) as catalyst or by simple heating at a temperature between 95 and 160° C.

The Huisgen reaction consequently makes it possible to connect, with covalent bond, a component A, B or Redox or its derivative comprising an azido group to an identical or different component comprising an acetylene group.

Mention may be made, as second example of a pair of functional groups L, of an $NH_2$ group and a COOH group which react together to form an amide group, according to the following reaction scheme:

A-$NH_2$ (or A-B—$NH_2$)+B—COOH(or Redox-COOH)→A-NH—CO—B, denoted A-B (or A-B—NH—CO-Redox, denoted A-B-Redox).

This type of reaction, referred to as an amidation or peptide reaction, is known to operate with a good yield using coupling agents (M. Kunishima et Tetrahedron, 2001, 57, 1551), such as 4-(4,6-dimethoxy-1,3,5-triazin-2-yl)-4-methylmorpholinium chloride or by simple heat treatment between 120° C. and 160° C. (Lukas J. Gooβen et al., Synthesis, 2009, 1, 160).

Palladium-based coupling methods which make possible the formation of a C—C bond and which give access to conjugated systems can also be envisaged in order to synthesize the compounds of formula (I) in which x=0 or 1. In this context, the Stifle, Suzuki, Heck and Sonogashira cou- pling reactions described below and well known to a person skilled in the art can be used.

X = I, Br, Cl, OTf
R = Ar, alkene

In these schemes, R and Ar represent A or A-B and R' or Ar' represent B or Redox.

Finally, in order to obtain the compounds of formula (I), it is also possible to envisage connecting the group A and the redox group by nucleophilic substitution reactions between a haloalkane precursor of the group A and a nucleophilic entity derived from the redox group, according to the following reaction scheme:

X = Cl, Br
Y = O, S

Another subject matter of the invention is the use of at least one compound of formula (I) as defined above as additive in an electrolyte composition of an electrochemical system having faradaic electrodes and/or pseudocapacitive or electric double-layer electrodes operating by circulation of ions between a positive electrode and a negative electrode separated by an electrolyte composition.

Another subject matter of the invention is thus an electrolyte composition for an electrochemical system having faradaic electrodes and/or pseudocapacitive or electric double-layer electrodes operating by circulation of ions between a positive electrode and a negative electrode separated by an electrolyte composition, said electrolyte composition being characterized in that it includes:
  at least one ionic compound,
  at least one liquid solvent, and
  at least one compound of formula (I) as defined above.

The amount of compound of formula (I) within the electrolyte composition in accordance with the invention preferably varies from $10^{-6}$ mol/l to $2 \times 10^{-1}$ mol/l and more preferably still from $10^{-4}$ mol/l to $10^{-1}$ mol/l.

According to a preferred embodiment of the invention, said electrolyte composition includes at least one compound of formula (I-1) as defined above.

According to a specific embodiment of the invention, the electrochemical system is a battery operating by circulation of lithium or sodium ions. In this case, the electrolyte generally comprises a lithium or sodium salt in solution in a polar aprotic solvent chosen in order to optimize the transportation and the dissociation of the ions.

Such salts can be chosen in particular from the lithium or sodium salts of an anion corresponding to one of the following formulae: $ClO_4^-$, $BF_4^-$, $PF_6^-$, $AsF_6^-$, $SbF_6^-$, $SCN^-$, $R_FSO_3^-$, $[(R_FSO_2)NSO_2R'_F]^-$, $[(R_FSO_2)C(Y)SO_2R_F']^-$ in which Y is CN or $SO_2R_F''$, $[R_FSO_2(NCN)]^-$, $[R_FSO_2\{C(CN)_2\}]^-$, 2-perfluoroalkyl-4,5-dicyanoimidazole $[R_FC_5N_4]^-$, 4,5-dicyano-1,2,3-triazole $[C_4N_5]^-$, 2,5-bis(fluorosulfonyl)-1,3,4-triazole $[C_2F_2S_2O_4]^-$ and 3-cyano-5-perfluoroalkyl-1,3,4-triazole $[R_FC_3N_4]^-$, $R_F$, $R_F'$ and $R_F''$ being alkyl groups in which at least 60% of the hydrogen atoms are replaced by fluorine atoms.

According to a preferred embodiment of the invention, the electrolyte comprises a lithium salt chosen from $LiPF_6$, $LiAsF_6$, $LiClO_4$, $LiBF_4$, $LiC_4BO_8$, $Li(C_2F_5SO_2)_2N$, $Li[(C_2F_5)_3PF_3]$, $LiCF_3SO_3$, $LiCH_3SO_3$, $LiN(SO_2CF_3)_2$ and $LiN(SO_2F)_2$.

The polar aprotic compounds of the liquid solvent of the electrolyte composition are preferably chosen from linear or cyclic carbonates, linear or cyclic ethers, linear or cyclic esters, linear or cyclic sulfones, sulfamides and nitriles. The solvent is preferably composed of at least two carbonates chosen from ethylene carbonate, propylene carbonate, dimethyl carbonate, diethyl carbonate and ethyl methyl carbonate.

According to another specific embodiment of the invention, the electrochemical system is a supercapacitor. In this case, the electrolyte composition can be chosen from:
  the electrolyte compositions comprising a lithium or sodium salt in solution in a polar aprotic solvent and as described above for the batteries;
  aqueous solutions of neutral pH (pH between 5 and 9 approximately), such as solutions of $K_2SO_4$ or of a salt of chlorate type;
  aqueous solutions of acidic pH (pH<5), such as sulfuric acid solutions;
  aqueous solutions of basic pH (pH>9), such as potassium hydroxide or sodium hydroxide solutions.

Finally, a subject matter of the invention is an electrochemical system having faradaic electrodes and/or pseudocapacitive or electric double-layer electrodes operating by circulation of ions between a positive electrode and a negative electrode separated by an electrolyte composition, characterized in that the electrolyte composition is as defined above and in that one and/or other of the electrodes comprises at least one material comprising hydroxyl functional groups and/or one carbon-based material and/or one carbon-based additive.

According to the invention, said system can in particular be a lithium battery, a sodium battery, an electric double-layer supercapacitor, a hybrid system comprising a battery electrode (faradaic electrode) and a supercapacitive electrode (pseudocapacitive or electric double-layer electrode) or alternatively a continuous flow electrochemical cell (flow cell).

When the system is a battery or a hybrid system comprising a positive battery electrode (faradaic electrode), said positive electrode is generally composed of a current collector carrying a positive electrode active material, optionally an electron conducting agent and optionally a binder. The content of active material of said composite material is preferably from 5% to 95% by weight, the content of electron conducting agent is preferably from 0.1% to 30% by weight and the content of binder is preferably less than 25% by weight.

In this case and when the electrochemical device in accordance with the invention operates by circulation of lithium ions, the active material of the positive electrode is preferably chosen from:

- transition metal oxides having a spinel structure of $LiM_2O_4$ type and transition metal oxides having a lamellar structure of $LiMO_2$ type in which M represents at least one metal chosen from the group consisting of Mn, Fe, Co, Ni, Cu, Mg, Zn, V, Ca, Sr, Ba, Ti, Al, Si, B and Mo;
- oxides having a polyanionic framework of $LiM_y(XO_z)_n$ type in which M represents at least one metal chosen from the group formed by Mn, Fe, Co, Ni, Cu, Mg, Zn, V, Ca, Sr, Ba, Ti, Al, Si, B and Mo and X represents an element chosen from the group consisting of P, Si, Ge, S and As;
- vanadium-based oxides of $V_2O_5$ and $LiV_3O_8$ types and their derivatives;
- manganese-based oxides of $MnO_2$ type and its derivatives;
- sulfur or phosphorus.

Preference is given, among the oxides having a spinel structure of $LiM_2O_4$ type, to those in which M represents at least one metal chosen from Mn and Ni. Preference is given, among the oxides having a lamellar structure of $LiMO_2$ type, to those in which M represents at least one metal chosen from Mn, Co and Ni. Preference is given in particular, among the oxides having a polyanionic framework of $LiM_y(XO_z)_w$ type, to phosphates having an olivine structure, the composition of which corresponds to the formula $LiMPO_4$ in which M represents at least one element chosen from Mn, Fe, Co and Ni. $LiFePO_4$ is preferred.

Still in this case and when the electrochemical device in accordance with the invention operates by circulation of sodium ions, the active material of the positive electrode is preferably chosen from:

- lamellar fluorophosphates $Na_2TPO_4F$ in which T represents a divalent element chosen from Fe, Mn, Co and Ni, which elements can be partially replaced by Mg or Zn, or a divalent ion VO;
- fluorosulfates $NaTSO_4F$ in which T' represents at least one element chosen from Fe, Mn, Co and Ni, a portion of which can be replaced by Mg, and a portion of the sulfate groups $SO_4^{2-}$ can be replaced by the isosteric and isocharge group $PO_3F^{2-}$;
- polysulfides $Na_2S_n$ ($1 \leq n \leq 6$), and the sodium salts of dimercaptothiadiazole and dimercaptooxazole;
- dithiocarbamates $Na[CS_2NR'R'']$ in which each of the R' and R'' groups represents a methyl, ethyl or propyl radical or else R' and R'' form a ring (for example, pyrrolidine or morpholine).

Among such positive electrode active materials, $Na_2FePO_4Fe$ and $NaFeSO_4F$ are preferred.

The electron conducting agent of the positive electrode is a carbon-based agent which can be chosen in particular from graphite, graphite carbon blacks, graphene, carbon nanofibers or carbon nanotubes.

As indicated above, the positive electrode can additionally comprise a binder, in particular a polymer binder, intended to ensure cohesion between the particles of the electrode active material and the electron conducting agent. Mention may in particular be made, among such polymer binders, of polysaccharides, modified polysaccharides, latexes, polyelectrolytes, polyethers, polyesters, polyacrylic polymers, polyurethanes, polyepoxides, polyphosphazenes, polysulfones or halogenated polymers.

Mention may more particularly be made, among such polymers, of polytetrafluoroethylene (PTFE), carboxymethylcellulose (CMC) or polyvinylidene fluoride (PVDF).

When the system is a battery or a hybrid system comprising a negative battery electrode (faradaic electrode), said negative electrode can in particular be composed of lithium metal (preferably in the film form), an alloy of lithium, graphite, carbon fibers, carbon nanotubes, acetylene black or alternatively a current collector carrying an electrode composite material comprising a negative electrode active material, such as silicon, tin, titanium oxides, Co or Cu oxides, and the like, optionally an electron conducting agent chosen from those defined above for the positive electrode, and optionally a binder.

When the system is a pseudocapacitive or electric double-layer supercapacitor, the positive and negative electrodes are generally composed of a porous carbon-based material chosen from graphite, graphite carbon blacks, graphene, carbon nanofibers or carbon nanotubes, said porous material being impregnated with the electrolyte composition. Said electrodes can additionally comprise an electrode active material chosen from certain oxides, such as manganese or ruthenium oxides, and nitrides.

In the hybrid systems, the positive and negative electrodes can be respectively chosen from the electrodes described above for the faradaic electrode systems and the supercapacitors.

The present invention is illustrated by the following implementational examples, to which, however, it is not limited.

DETAILED DESCRIPTION

EXAMPLES

Example 1

Synthesis of the Compound of Formula (I-1)

The synthesis of the compound of formula (I-1) was carried out according to the following synthetic scheme:

The NMR spectra were recorded on a Bruker Avarice III 300 device ($^1$H, 300 MHz and $^{13}$C, 75 MHz).

The chemical shifts are expressed as parts per million (ppm) with respect to TMS.

The infrared spectra were recorded on a Bruker Vertex 70 spectrometer.

Matrix-assisted laser desorption/ionization was carried out on a MALDI-TOF MS Biflex III Bruker Daltonics spectrometer with dithranol for matrix.

The electrospray ionization (ESI) mass spectra were recorded using a RAS Jeol 700 spectrometer.

1) First Stage: Synthesis of Compound 1

Thionyl chloride (0.8 ml, 11 mmol) was slowly added, under a nitrogen atmosphere, using a syringe, to a solution, placed in a 50 ml three-necked round-bottom flask, of 4-(pyren-1-yl)butanoic acid (2 g, 6.94 mmol) in anhydrous CHCl$_3$ (20 ml). The reaction mixture was maintained at reflux for 2 h, then cooled to ambient temperature and concentrated under vacuum. 20 ml of CH$_2$Cl$_2$ were then added to the mixture and the solvent was evaporated under vacuum in order to remove the excess thionyl chloride. This procedure was repeated twice and made it possible to obtain the intermediate acyl chloride.

A solution of this intermediate in anhydrous CHCl$_3$ (20 ml) was added dropwise, under a nitrogen atmosphere, to a solution of 4-azidoaniline hydrochloride (1.2 g, 7.03 mmol) in anhydrous CHCl$_3$ (20 ml) and in the presence of triethylamine (2 ml, 14.4 mmol). The reaction mixture was stirred for 15 h, resulting in the formation of a white-grey precipitate. The solvent was evaporated and the crude product was extracted with warm ethylacetate (EtOAc) (3×250 ml). The extracts were combined, washed with a saturated aqueous NaCl solution (2×150 ml), dried over MgSO$_4$ and concentrated to give compound 1 in the form of a beige powder (2.54 g, yield 91%).

Melting point: 176-177° C.

$^1$H NMR (300 MHz, d$_6$-DMSO) δ: 9.99 (br. s, 1H, N—H), 8.41 (d, 1H, $^3$J=9.3 Hz), 8.29-8.20 (m, 4H), 8.15 (d, 1H, $^3$J=9.1 Hz), 8.12 (d, 1H, $^3$J=9.1 Hz), 8.06 (t, 1H, $^3$J=7.7 Hz), 7.97 (d, 1H, $^3$J=7.7 Hz), 7.65 (d, 2H, $^3$J=8.7 Hz), 7.06 (d, 2H, $^3$J=8.7 Hz), 3.38 (t, 2H, $^3$J=7.5 Hz), 2.46 (t, 2H, $^3$J=7.2 Hz), 2.11 (quint., 2H, $^3$J=7.5 Hz).

IR: $\tilde{v}$=3253 cm$^{-1}$ (N—H), 2116 cm$^{-1}$ (—N$_3$), 1655 cm$^{-1}$ (C=O).

ESI$^-$ MS: 439.4 [M+Cl$^-$], 842.8 [2M+Cl$^-$].

2) Second Stage: Synthesis of the Compound of Formula (I-1)

107.8 μl of N,N-diisopropylethylamine (DIPEA, 0.65 mmol) and 7.3 mg of CuI (0.04 mmol) were added to a solution of compound 1 obtained above in the preceding stage (100 mg, 0.25 mmol) and 52 mg of ethynylferrocene (0.25 mmol) in CH$_3$CN (7.5 ml). The mixture was stirred at ambient temperature for 5 days, After diluting in EtOAc (100 ml), the organic phase was washed with a saturated aqueous NaCl solution (2×20 ml), dried over MgSO$_4$ and concentrated under vacuum, making it possible to obtain a slightly brown powder.

Melting point: 270-272° C.

$^1$H NMR (300 MHz, d$_5$-pyridine) δ: 11.01 (br. s, 1H, N—H), 8.44 (d, 1H, $^3$J=9.3 Hz), 8.26–7.94 (m, 12H), 7.87

(d, 1H, $^3J$=7.8 Hz), 5.03 (br, s, 2H, Fc), 4.35 (br. s, 2H, Fc), 4.16 (br. s. 5H, Fe), 3.47 (t, 2H, $^3J$=7.5 Hz), 2.63 (t, 2H, $^3J$=7.2 Hz), 2.40 (quint., 2H, $^3J$=7.2 Hz).

IR: $\tilde{\nu}$=3347 cm$^{-1}$ (N—H), 1670 cm$^{-1}$ (C=O).

MALDI-TOF MS: 613.8 [M$^+$].

Example 2

Preparation of an Electrochemical Cell

In this example, an electrochemical cell comprising a working electrode (positive electrode), comprising carbon nanotubes, and a counterelectrode (negative electrode) consisting of a sheet of lithium metal rolled onto a current collector made of stainless steel and of a sintered glass sheet as separator, was prepared, the assembly being immersed in a liquid electrolyte.

The working electrode (3 mg) was prepared by manual mixing of stripped multi-walled carbon nanotubes (MW-CNT), sold under the trade name MWNT (95+ %, OD 20-30 nm) by Nanostructured & Amorphous Materials Inc. (Nano-Amor), according to the process described in the patent application FR 2 935 546, and of polytetrafluoroethylene, sold under the trade name Teflon® by Aldrich, in a respective ratio by weight of 95/5. The mixture obtained was compressed at 10 tonnes/cm$^2$ on a stainless steel grid.

The two electrodes were placed in an electrolyte consisting of a 1M solution of LiPF$_6$ dissolved in a mixture of ethylene carbonate (EC) and dimethyl carbonate (DMC) (1/1 (v/v)) and are on either side of a reference electrode consisting of lithium metal immersed in the same electrolyte and separated by a sintered glass sheet.

The system was cycled 5 times at 50 mV/s (88 s/cycle) in order to test the connections before dissolving, in the electrolyte, 0.625 mg of the redox compound of formula (I-1), as synthesized above in example 1, per 5 ml of electrolyte.

After addition of the compound of formula (I-1), the system was subjected to cycling under the same conditions.

The capacity of the working electrode was determined, before and after addition of the compound of formula (I-1), by coulometry.

Before addition of the compound of formula (I-1), the capacity of the working electrode was approximately 0.015 mAh (5 mAh/g). This capacity corresponds to the double-layer capacity of the conducting agent (7 F/g). It is deduced therefrom that the electrochemically active surface of the electrode is approximately 87 m$^2$/g, taking 10 µF/g as reference for the double-layer capacity. This value is in good agreement with the BET specific surface of the initial carbon nanotubes, which is of the order of 110 m$^2$/g.

Figure 1:
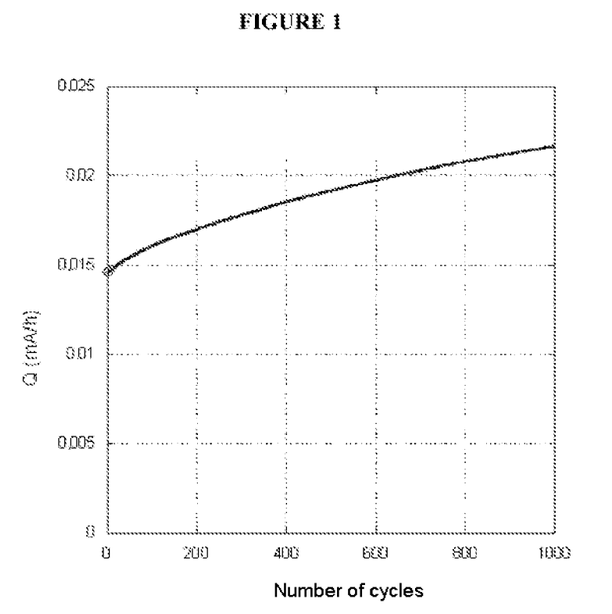
FIG. 1 is a graph of the discharge Q (mA·h) expressed as a function of the number of cycles, in accordance with Example 2.

The change in the capacity of the electrode was monitored for at least 24 hours and is given in the appended FIG. 1, in which the discharge Q (mA.h) is expressed as a function of the number of cycles, the circle on the curve representing the moment where the compound of formula (I-1) was added to the electrolyte.

It is found, in this figure, that, from the addition of the compound of formula (I-1), the capacity of the electrode increased to reach 0.022 mA·h after 1000 cycles, i.e. approximately 24 hours.

Figure 2:
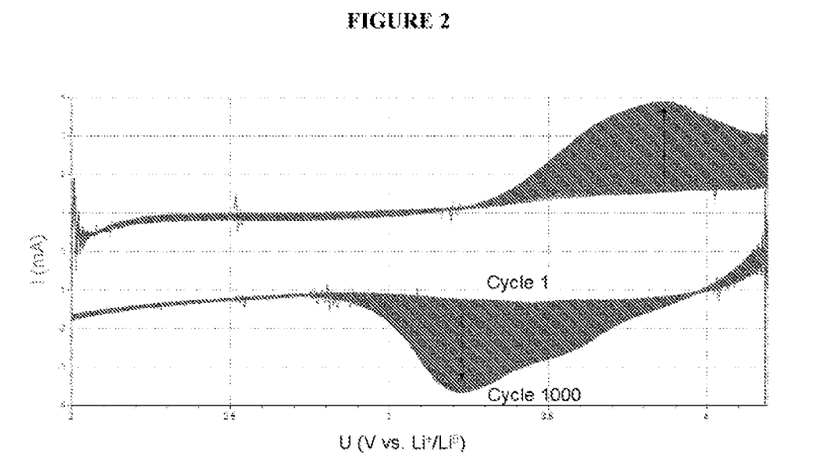
FIG. 2 shows the growth of a redox wave at approximately 3.25 V in discharge and 3.85 V in charge, in which intensity of the current I (mA) is a function of the potential (in volts) vs $Li^+/Li^0$), in accordance with Example 2.

This increase in capacity occurs subsequent to the faradaic activation of the electrode, which is reflected by the growth of a redox wave at approximately 1.25 V in discharge and 3.85 V in charge (see the appended FIG. 2, in which the intensity of the current I (mA) is a function of the potential (in volts) vs Li$^+$/Li$^0$).

This signal indicates that the compound of formula (I-1) is permanently attached to the conducting agent, in this instance the carbon nanotubes, thus making it possible to store/deliver approximately 1.5 times more energy and power than an initially (16 Wh/kg$_{electrode}$, 1.3 kW/kg$_{electrode}$, versus 23 Wh/kg$_{electrode}$, 1.9 kW/kg$_{electrode}$), correction made for the weight of grafted molecule.

This result demonstrates that the faradaic activation of the electrode can be carried out during the cycling. The amount of compound of formula (I-1) grafted is of the order of 1.5×10$^{-11}$ mol/cm$^2$, which corresponds to a mean grafting rate of the order of 0.06×10$^{-11}$ mol/cm$^2$/hour. It should be noted that the grafting of the compound of formula (I-1) does not detrimentally affect the double-layer capacity.

Example 3

A working electrode of 1 mg, otherwise identical in every respect to that prepared above in example 2, was immersed for 120 hours in a 2×10$^{-4}$ mol/l solution of the compound of formula (I-1) in the initial electrolytic solution.

After immersion, the electrode was cycled according to the same setup and under the same conditions as those set out above in example 2. In this case, the initial capacity of the electrode reached 0.011 mAh at 100 mV/s (44 s/cycle), whereas it was only 0.006 mAh initially, thus making it possible to store/deliver twice as much energy and power than initially (19 Wh/kg$_{electrode}$, 3 kW/kg$_{electrode}$ versus 35 Wh/kg$_{electrode}$, 6 kW/kg$_{electrode}$), for at least 1000 cycles.

This result demonstrates that the faradaic activation of the electrode can be carried out before the cycling. The amount of compound of formula (I-1) attached was of the order of 6.8×10$^{-11}$ mol/cm$^2$, which is lower than the expected value (7.2 mol/cm$^2$), in view of the amount dissolved and for a grafting rate determined at 0.06 10$^{-11}$ mol/cm$^2$/hour in example 2. This result indicates that saturation of the surface is reached. The only limitation on the increase in the performance obtained by using a compound of formula (I) as additive in an electrolyte thus appears to be the surface area developed by the conducting agent of the electrode, Example 4

In this example, an electrochemical cell identical to that prepared above in example 2 was prepared but while replacing the carbon nanotubes with carbon fibers sold under the trade name CFx by Showa Denko K.K., in an electrode of 0.95 mg.

The electrode was subsequently tested in cycling as described above in example 2, before and after addition of the compound of formula (I-1).

After addition of the compound of formula (I-1), the capacity of the electrode was approximately 0.012 mAh (13 mAh/g), this capacity corresponding to the double-layer capacity of the conducting agent (19 F/g). It was deduced therefrom that the electrochemically active surface of the electrode was approximately 190 m$^2$/g, taking 10 µF/g as reference for the double-layer capacity.

This value was in good agreement with the BET specific surface of the initial carbon fibers, which is of the order of 245 m$^2$/g.

From the addition of the compound of formula (I-1), the capacity increased to reach 0.033 mAh (30 mAh/g) after 8600 cycles, i.e. approximately 115 hours.

Figure 3:
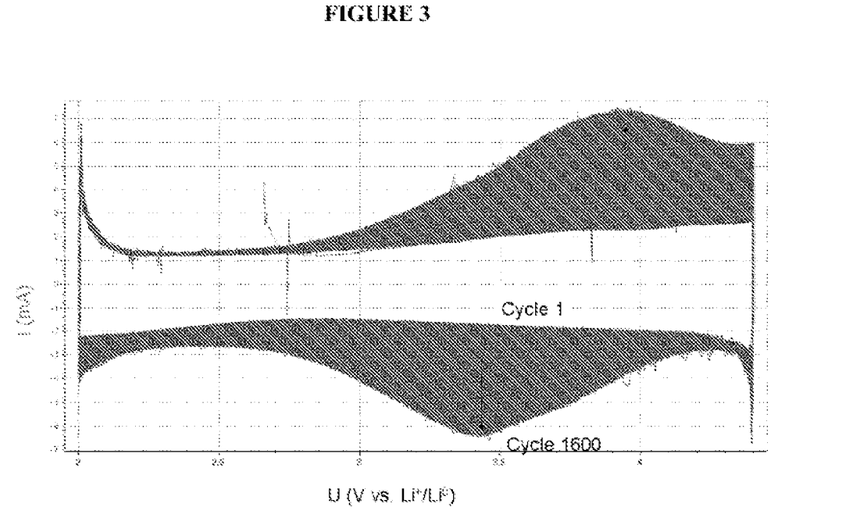
FIG. 3 shows the growth of a redox wave at approximately 3.45 V, in which the intensity of the current I (mA) is a function of the potential (in volts) vs $Li^+/Li^0$), in accordance with Example 4.

This increase in capacity occurs subsequent to the faradaic activation of the electrode, which is reflected by the growth of a redox wave at approximately 3.45 V (see appended FIG. 3, in which the intensity of the current I (mA) is a function of the potential (in volts) vs $Li^+/Li^0$).

This signal indicates that the compound of formula (I-1) is permanently attached to the carbon fibers, thus making it possible to store/deliver close to 2.5 time more energy and specific power than initially (40 $Wh/kg_{electrode}$, 6 $kW/kg_{electrode}$, versus 100 $Wh/kg_{electrode}$, 15 $kW/kg_{electrode}$), correction made for the weight of the compound of formula (I-1) grafted.

The amount of compound of formula (I-1) grafted is of the order of $8.6 \times 10^{-11}$ mol/cm², which corresponds to a mean grafting rate of the order of $0.075 \times 10^{-11}$ mol/cm²/hour, which is approximately 20% greater than that observed above in example 2 when employing an electrode prepared from carbon nanotubes. It should be noted that the grafting of the compound of formula (I-1) does not detrimentally affect the double-layer capacity. This result demonstrates that the energy and specific power gains introduced by the compound of formula (I-1) are proportional to the surface area developed by the conducting agent of the electrode and depend on its nature, the better time/performance efficiency being obtained with the carbon fibers.

Example 5

A working electrode analogous to that used above in example 4 was cycled for 3750 cycles under the same conditions as that of example 4.

By way of comparison, an electrode in every respect identical was also cycled for 3750 cycles in an electrolyte devoid of compound of formula (I-1).

Figure 4:
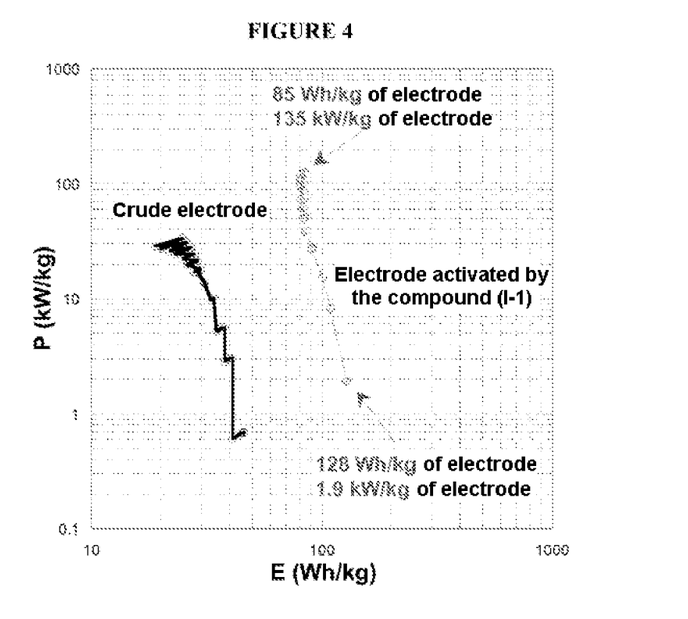
FIG. 4 shows the results of a specific power test carried out on each of the electrodes in accordance with Example 5.

The results of a specific power test carried out on each of the electrodes are given in the appended FIG. 4, which represents the Ragone diagram of the electrodes tested. In this figure, the specific power (P), expressed in kW/kg, is a function of the power density (E), expressed in Wh/kg. The curve in a thick black line corresponds to the controlled electrode cycled in a conventional electrolyte, that is to say not comprising the compound of formula (I-1), and the curve in a thin black line corresponds to the electrode cycled in the electrolyte in accordance with the invention, that is to say comprising the compound of formula (I-1).

These results show that, when an electrolyte in accordance with the invention, that is to say including a compound of formula (I-1), is used, an electrode of 1 mg is capable of delivering 85 $Wh/kg_{electrode}$ (0.425 $mWh/m^2_{electrode}$) in 2.4 seconds, i.e. a power of approximately 130 $kW/kg_{electrode}$ (0.65 $mW/m^2_{electrode}$). The same electrode, cycled in a conventional electrolyte, shows a performance which is approximately 5 times inferior.

These performances constituent, to the knowledge of the inventors, the best energy/power compromise ever obtained for electrodes having a high charge (10 mg/cm²).

The use of an electrolyte in accordance with the invention thus makes it possible, in addition to all the abovementioned advantages, to obtain an object capable of simultaneously delivering great energy and great power, which represents the combined advantages of the supercapacitors and batteries.

The invention claimed is:

1. An electrolyte composition for an electrochemical system having faradaic electrodes and/or pseudocapacitive or electric double-layer electrodes operating by circulation of ions between a positive electrode and a negative electrode separated by an electrolyte composition, said electrolyte composition being characterized in that it includes:
at least one ionic compound,
at least one liquid solvent,
at least one compound of formula (I):

$$A-(B)_x-\text{Redox} \quad (I)$$

in which:
A represents a group capable of being chemisorbed at the surface of carbon-based materials or materials comprising a carbon-based additive, said groups being selected from the group consisting of pyrene, perylene, anthracene, triphenylene, coronene, fluorene and azulene groups;
x is 0 or 1
B represents a connecting arm chosen from aromatic groups, heterocycles and linear $C_1$-$C_{100}$ alkyl chains optionally comprising one or more heteroatoms, one or more functional groups, and/or one or more aromatic rings and/or one or more heterocycles;
Redox represents a redox group comprising one or more redox functional groups.

2. The composition as claimed in claim 1, wherein the amount of compound of formula (I) within the electrolyte composition varies from $10^{-6}$ mol/l to $2 \times 10^{-1}$ mol/l.

3. The composition as claimed in claim 1, wherein said composition includes at least one compound of formula (I-1)

(I-1)

4. The composition as claimed in claim 1, wherein the electrochemical system is a battery operating by circulation of lithium or sodium ions and in that the electrolyte comprises a lithium or sodium salt in solution in a polar aprotic solvent.

5. The composition as claimed in claim 4, wherein the electrolyte comprises a lithium salt selected from the group consisting of $LiPF_6$, $LiAsF_6$, $LiClO_4$, $LiBF_4$, $LiC_4BO_8$, $Li(C_2F_5SO_2)_2N$, $Li[(C_2F_5)_3PF_3]$, $LiCF_3SO_3$, $LiCH_3SO_3$, $LiN(SO_2CF_3)_2$ and $LiN(SO_2F)_2$.

6. The composition as claimed in claim 1 wherein the electrochemical system is a supercapacitor and in that the ionic compound and the liquid solvent are selected from the group consisting of:
a lithium or sodium salt in solution in a polar aprotic solvent;
aqueous solutions of neutral pH selected from the group consisting of solutions of $K_2SO_4$ and of a salt of chlorate type;
aqueous solutions of acidic pH, selected from the group consisting of sulfuric acid solutions; and
aqueous solutions of basic pH, selected from the group consisting of potassium hydroxide and sodium hydroxide solutions.

7. An electrochemical system having faradaic electrodes and/or pseudocapacitive or electric double-layer electrodes operating by circulation of ions between a positive electrode and a negative electrode separated by an electrolyte composition, wherein the electrolyte composition is as defined in claim 1 and in that one and/or other of the electrodes comprises at least one material comprising one carbon-based material and/or one carbon-based additive.

8. The system as claimed in claim 7, wherein said system is a lithium battery, a sodium battery, an electric double-layer supercapacitor, a hybrid system comprising a battery electrode and a supercapacitor electrode, or a continuous flow electrochemical cell.

9. The composition as claimed in claim 1, wherein said heteroatoms are O, N or S.

10. The composition as claimed in claim 1, wherein said functional groups are an amide or ester functional group.

11. The composition as claimed in claim 1, wherein the redox group of the compounds of formula (I) is selected from the group consisting of ferrocene,(2,2,6,6-tetramethyl-piperidin-1-yl)oxyl, porphyrin, oligothiophene, S-bithiophene-S-methyl, oligo-3,4-ethylenedioxythiophene, oligopolyaniline, oligopyrrole, anthracene and catechol groups and rhodizonate salts.

* * * * *